United States Patent
Jascob et al.

(10) Patent No.: US 6,636,757 B1
(45) Date of Patent: Oct. 21, 2003

(54) METHOD AND APPARATUS FOR ELECTROMAGNETIC NAVIGATION OF A SURGICAL PROBE NEAR A METAL OBJECT

(75) Inventors: Bradley Jascob, Broomfield, CO (US); David Simon, Boulder, CO (US); Paul Kessman, Boulder, CO (US); Aaron Smith, Denver, CO (US)

(73) Assignee: Surgical Navigation Technologies, Inc., Louisville, CO (US)

( * ) Notice: Subject to any disclaimer, the term of this patent is extended or adjusted under 35 U.S.C. 154(b) by 96 days.

(21) Appl. No.: 09/873,604

(22) Filed: Jun. 4, 2001

(51) Int. Cl.[7] .................................................. A61B 5/05
(52) U.S. Cl. .................. 600/424; 600/423; 324/207.15; 324/207.11; 324/207.13
(58) Field of Search .................. 600/424, 422, 600/423; 324/207.12, 207.17, 225, 208, 207.11; 128/899

(56) References Cited

U.S. PATENT DOCUMENTS

| 4,849,692 A | 7/1989 | Blood |
| 4,945,305 A | 7/1990 | Blood |
| 5,744,953 A | 4/1998 | Hansen |
| 5,767,669 A | 6/1998 | Hansen et al. |
| 6,172,499 B1 | 1/2001 | Ashe |
| 6,246,231 B1 | 6/2001 | Ashe |
| 6,437,567 B1 * | 8/2002 | Schenck et al. ............. 324/318 |

* cited by examiner

*Primary Examiner*—Mark Paschall
(74) *Attorney, Agent, or Firm*—Harness, Dickey & Pierce, P.L.C.

(57) ABSTRACT

A method and apparatus for electromagnetic navigation of a surgical probe near a metal object. The electromagnetic navigation system includes a transmitter coil array and a shield. The transmitter coil array has a plurality of transmitter coils and is operable to generate the electromagnetic field to navigate the probe. The shield is positioned adjacent the metal object and is operable to shield the metal object from the electromagnetic field generated by the transmitter coil array, such that the shield substantially reduces distortion of the electromagnetic field by the metal object.

55 Claims, 10 Drawing Sheets

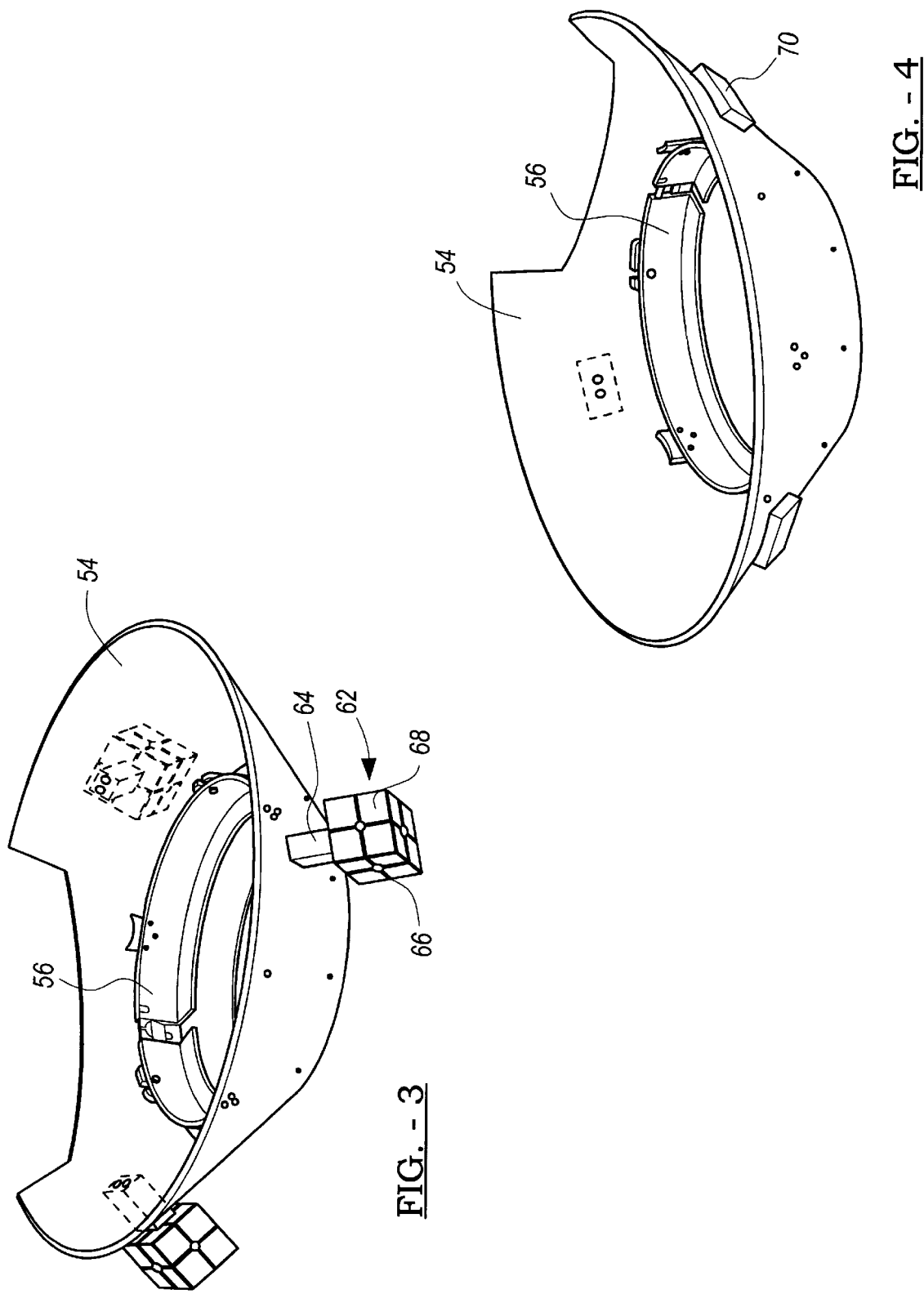

METHOD AND APPARATUS FOR ELECTROMAGNETIC NAVIGATION OF A SURGICAL PROBE NEAR A METAL OBJECT

FIELD OF THE INVENTION

This invention relates generally to navigation of a probe and, more particularly, to a method and apparatus for electromagnetic navigation of a surgical probe near a metal object.

BACKGROUND OF THE INVENTION

Various systems currently exist, which assist in guiding and navigating a surgical probe through a patient undergoing a surgical procedure. These systems include, for example, fluoroscopic, ultrasonic, conductive, optical and electromagnetic type navigation systems.

Various electromagnetic type navigation systems have already been proposed, such as that disclosed in U.S. Pat. No. 4,821,731 to Martinelli, et al., U.S. Pat. No. 5,592,939 to Martinelli and U.S. Pat. No. 5,913,820 to Bladen, et al., which are each hereby incorporated by reference. Advantages of such electromagnetic tracking navigation systems are significant over existing navigation systems. For example, low-frequency electromagnetic waves are not attenuated by the body and therefore, there are no "line-of-sight" issues as with existing optical systems. The transmitter coil array may also be placed underneath or above the patient and the navigated surgical instrument or probe may be used above or below the transmitter coil array. The receiver coils utilized in the surgical instrument or probe are also generally much smaller than existing type navigation systems, which may enable surgical procedures that were previously impossible due to instrument size. The small size of the receiver coils also enable the receiver coils to be placed near the tip of the instrument providing further accuracy and the ability to navigate non-rigid instruments.

However, electromagnetic type navigation systems do have the disadvantage that the electromagnetic field may be distorted by metal objects, sometimes referred to as metallic distortions. In this regard, metal objects that are generally large in size cause the magnetic field to bend, thereby possibly causing inaccuracy in the reported probe position. The other effect of positioning a metal object near the electromagnetic field being navigated is conduction effects. For example, a metal object positioned near or in the electromagnetic field, such as a fluoroscope (C-arm) or an OR table, may create a virtual coil along the metal surface that creates an interference back into the magnetic field. Again, this may create an inaccuracy in the reported probe position because the exact field strengths in the previously known electromagnetic fields have been altered due to the metal object.

In order to reduce or eliminate the effects of distortion due to metal objects, known mathematical models of the electromagnetic fields produced by the transmitter coil array may be utilized. If these mathematical models are accurate, they can be used to represent a set of "known" fields used during the navigation process. However, the disadvantage with using mathematical models for the transmitted fields is that there are inherent inaccuracies in the manufacturing process of the transmitting coils in the transmitting coil array, which can lead to incorrect field values, which are mathematically modeled. These incorrect field values may lead to inaccuracy in the overall navigation process. The mathematical models are also generally very mathematically complex, and may, therefore, take an unreasonable amount of time for a computer to calculate and process.

What is needed then is a method and apparatus for electromagnetic navigation of a surgical probe near a metal object, which does not suffer from the above-mentioned disadvantages. This will, in turn, provide electromagnetic navigation of a surgical probe near a metal object that has greater accuracy, provide a shield to reduce or eliminate the effects of the metal object, provide a universal connection to connect the shield to the metal object, provide a calibration process that takes into effect either the shield or the metal object, provide a set of transmitting coils, which may be attached to the shield, integrated into the shield or integrated into the metal object itself, and provide wireless communications in the electromagnetic navigation system for ease of assembly into existing hardware. It is, therefore, an object of the present invention to provide such a method and apparatus for electromagnetic navigation of a surgical probe near a metal object.

SUMMARY OF THE INVENTION

In accordance with the teachings of the present invention, a method and apparatus for electromagnetic navigation of a surgical probe near a metal object is provided.

In one embodiment, an electromagnetic navigation system for use in navigating a probe through an electromagnetic field positioned near a metal object includes a transmitter coil array and a shield. The transmitter coil array has a plurality of transmitter coils and is operable to generate the electromagnetic field to navigate the probe. The shield is positioned adjacent the metal object and is operable to shield the metal object from the electromagnetic field generated by the transmitter coil array, wherein the shield substantially reduces distortion of the electromagnetic field by the metal object.

In another embodiment, an electromagnetic navigation system for use in navigating a probe through an electromagnetic field during a surgical procedure includes a metal instrument and a transmitter coil array. The metal instrument is used during a surgical procedure and is formed at least in part by metallic material. The transmitter coil array has a plurality of transmit coils and is operable to generate the electromagnetic field used to navigate the probe. The transmitter coil array is integrated into the metal instrument, wherein the effects of metallic distortion on the electromagnetic field by the metal instrument is characterized during a calibration process to provide substantially accurate navigation of the probe during the surgical procedure.

In another embodiment, a method for calibrating an electromagnetic navigation system having a transmitter coil array that generates an electromagnetic field is provided. This method includes positioning the electromagnetic navigation system in a working environment to account for metallic distortion caused by a metallic object adjacent to the electromagnetic field, positioning a calibration sensor at a first calibration point, energizing a first coil in the transmitter coil array to generate a first field, sensing the first field strength in the first field with the calibration sensor, and repeating the positioning, energizing and sensing at a second calibration point, wherein effects of metallic distortion caused by the metallic object is taken into account during the calibration process.

Use of the present invention provides a method and apparatus for electromagnetic navigation of a probe through an electromagnetic field near a metal object. As a result, the aforementioned disadvantages associated with the currently available techniques have been substantially reduced or eliminated. Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Still other advantages of the present invention will become apparent to those skilled in the art after reading the following specification and by reference to the drawings in which:

FIG. 3 is a perspective view of a shield having extended transmitter coils according to the teachings of one embodiment of the present invention;

FIG. 4 is a perspective view of a shield having integrated transmitter coils according to the teachings of another embodiment of the present invention;

DETAILED DESCRIPTION OF THE PREFERRED EMBODIMENTS

The following description of the preferred embodiments concerning a method and apparatus for electromagnetic navigation of a surgical probe near a metal object is merely exemplary in nature and is not intended to limit the invention or its application or uses. Moreover, while the present invention is described in detail in association with a fluoroscope (C-arm) or an operating room (OR) table, those skilled in the art will readily understand that the present invention may be employed in many other environments having metal objects.

Figure 1:
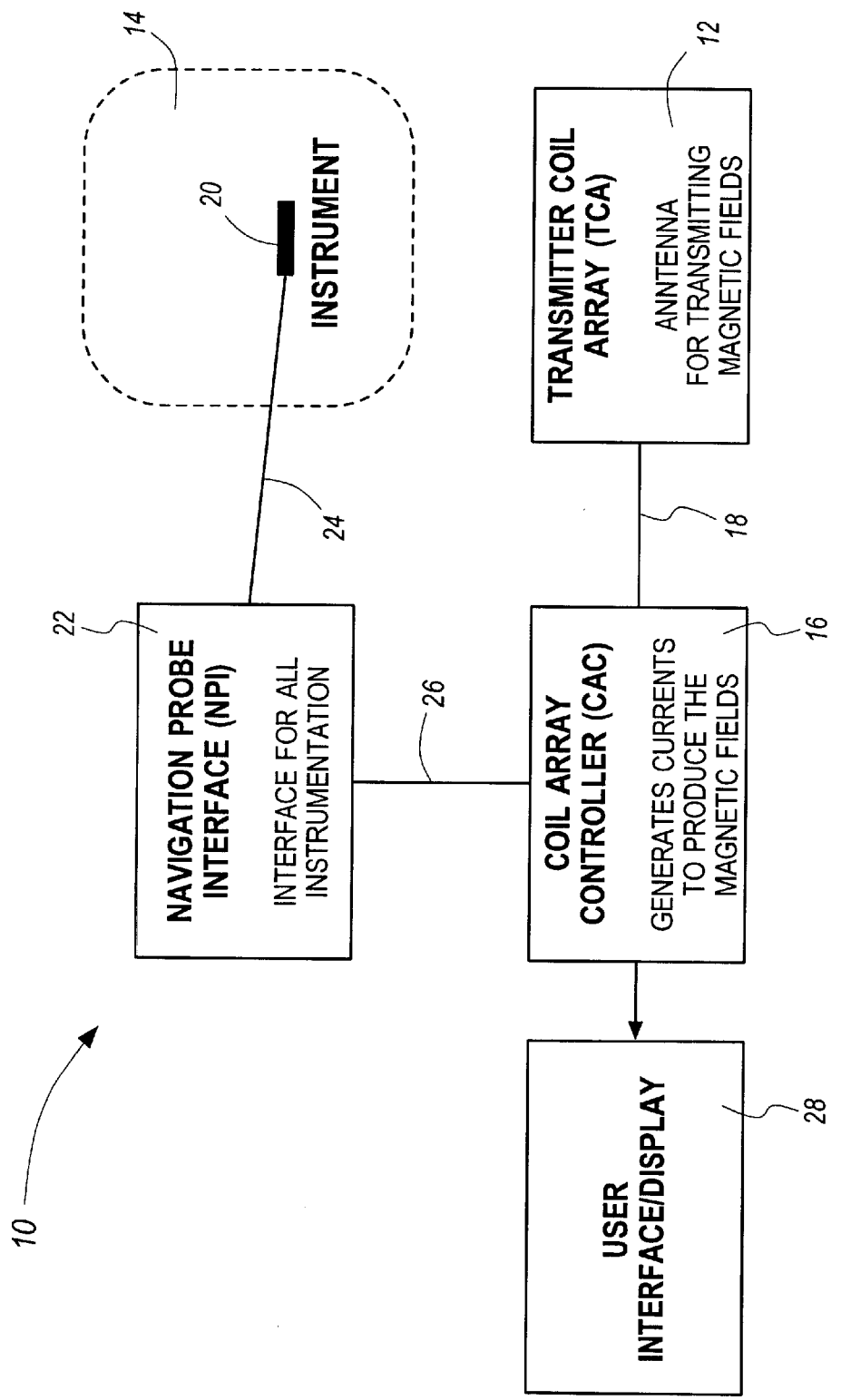
FIG. 1 is an electromagnetic navigation system block diagram according to the teachings of one embodiment of the present invention.

Referring to FIG. 1, an electromagnetic navigation system 10 according to the teachings of one embodiment of the present invention is shown. The electromagnetic navigation system 10 is implemented utilizing a transmitter coil array (TCA) 12, which emits low energy, low frequency AC signals to generate an electromagnetic field or region 14 adjacent to the transmitter coil array 12. The transmitter coil array 12 includes a plurality of coils, further discussed herein, which are driven by a coil array controller (CAC) 16. The coil array controller 16 sources AC current to drive each coil housed within the transmitter coil array 12, via transmission lines 18. The coil array controller 16 may drive the coils housed within the transmitter coil array 12 either sequentially, via time division, or simultaneously, via frequency division, or a combination of both. The electromagnetic field 14 generated by the transmitter coil array 12 provides very accurate known magnetic field strengths over the field of view (FOV) of the electromagnetic navigation system 10. Because the low-frequency electromagnetic waves generated by the transmitter coil array 12 are not attenuated by the body of a patient, there are no line-of-sight issues as with currently available optical systems.

An instrument 20, such as, but not limited to, a surgical probe, catheter, steerable catheter, endoscope, shunt, drill guide, awl/tap, orthopedic implant instrument, etc. located or positioned within the electromagnetic field 14 is able to detect the electromagnetic signal and measure the magnetic field strength by way of small loops of wire or receive coils attached to the instrument 20. The receive coils may be any diameter but are generally made small, for example, about one millimeter to about two millimeters in diameter, which provides for a much smaller instrument 20 than other existing instruments used in navigation systems, such as optically navigated systems. Because of the reduced size of the receiver coils, this enables the receiver coils to be placed near the distal tip of the instrument 20, thereby further reducing accuracy concerns that exist when the receiver coils are positioned more proximally in the instrument 20, since the instrument 20 may bend during navigation. The instrument 20 may include a single receiver coil consisting of multiple loops of wire or a single loop of wire and may also include multiple receiver coils to provide further positional information regarding the instrument 20, as is known in the art and further discussed herein.

The magnetic field strengths sensed by the instrument 20 are received by a navigation probe interface (NPI) 22, via a transmission line 24. The navigation probe interface 22 gathers the magnetic field strengths received by the instrument 20 and processes this information in order to identify the magnetic field strength generated by each coil in the transmitter coil array 12. The navigation probe interface 22 is able to track up to any number of coils, located in the transmitter coil array 12 based on the number of input ports provided, at a sampling rate of about thirty frames per second. The navigation probe interface 22 also directs or triggers the coil array controller 16 to drive each coil located in the transmitter coil array 12 either in a time multiplexed manner, frequency multiplexed manner or a combination of both. The navigation probe interface 22 is generally configured as a digital signal processor (DSP), but may also be configured as discrete logic circuits or any other type of electrical processor. The navigation probe interface 22 is also capable of supporting multiple instruments 20 in a multiplexed manner should this be desirable for the particular surgical procedure.

Once the magnetic field strengths of all the transmitting coils in the transmitter coil array 12 are measured and processed by the navigation probe interface 22, this field strength information is forwarded to the coil array controller 16, via transmission line 26. A general purpose computer or PC incorporated into the coil array controller 16 is then applied to "look-up" the single point in space where the field strengths detected by the receiver coil in the instrument 20 is equivalent to the known field strengths transmitted by the transmitter coil array 12. In this regard, the magnetic field strengths measured by the instrument 20 identify a unique position and orientation in space to determine the X, Y, Z point and the angle and azimuth of the receiver coil located in the instrument 20. Should rotation about the axis of the receiver coil positioned in the instrument 20 be desired, a second receiver coil may be required in the instrument 20. The process used by the coil array controller 16 employs known minimization techniques, such as Newton's method, further discussed herein.

Thus, the electromagnetic navigation system 10 is able to support electromagnetic navigation of the instrument 20 by generating electromagnetic fields from the transmitter coil array 12 throughout the region 14. Instrument 20 measures the magnetic field strengths by way of an electromagnetic sensor or receiver coil. Through design of these electromagnetic fields generated by each coil in the transmitter coil array 12, every position and orientation of each field generated has a unique set of electromagnetic field strengths that is known in the art. These electromagnetic levels or magnetic field strengths generate a system of equations that can be solved mathematically to determine the position and orientation of the instrument 20, as is known in the art.

The localized information which is determined in the coil array controller 16 is then forwarded to an application specific user interface/display 28. The user interface/display 28 may consist of a general purpose computer and a video display to provide image guidance to a surgeon with real time visual feedback of the surgery or navigation being performed. The user interface/display 28 may be configured to provide application specific interfaces for various surgical procedures, such as, but not limited to, cranial, 3-D spine, virtual fluoroscopy, cranial biopsies, tumor resections, craniotomies/craniectomies, thalamotomies/pallidotomies, spinal implant procedures, such as pedicle screw placement, sinus procedures, such as maxillary antrostomies, ethmoidectomies, sphenoidotomies/sphenoid explorations, turbinate resections, and frontal sinusotomies, cardiac mapping procedures, cardiac lead placements, orthopedic, interventional radiology, etc.

Figure 2:
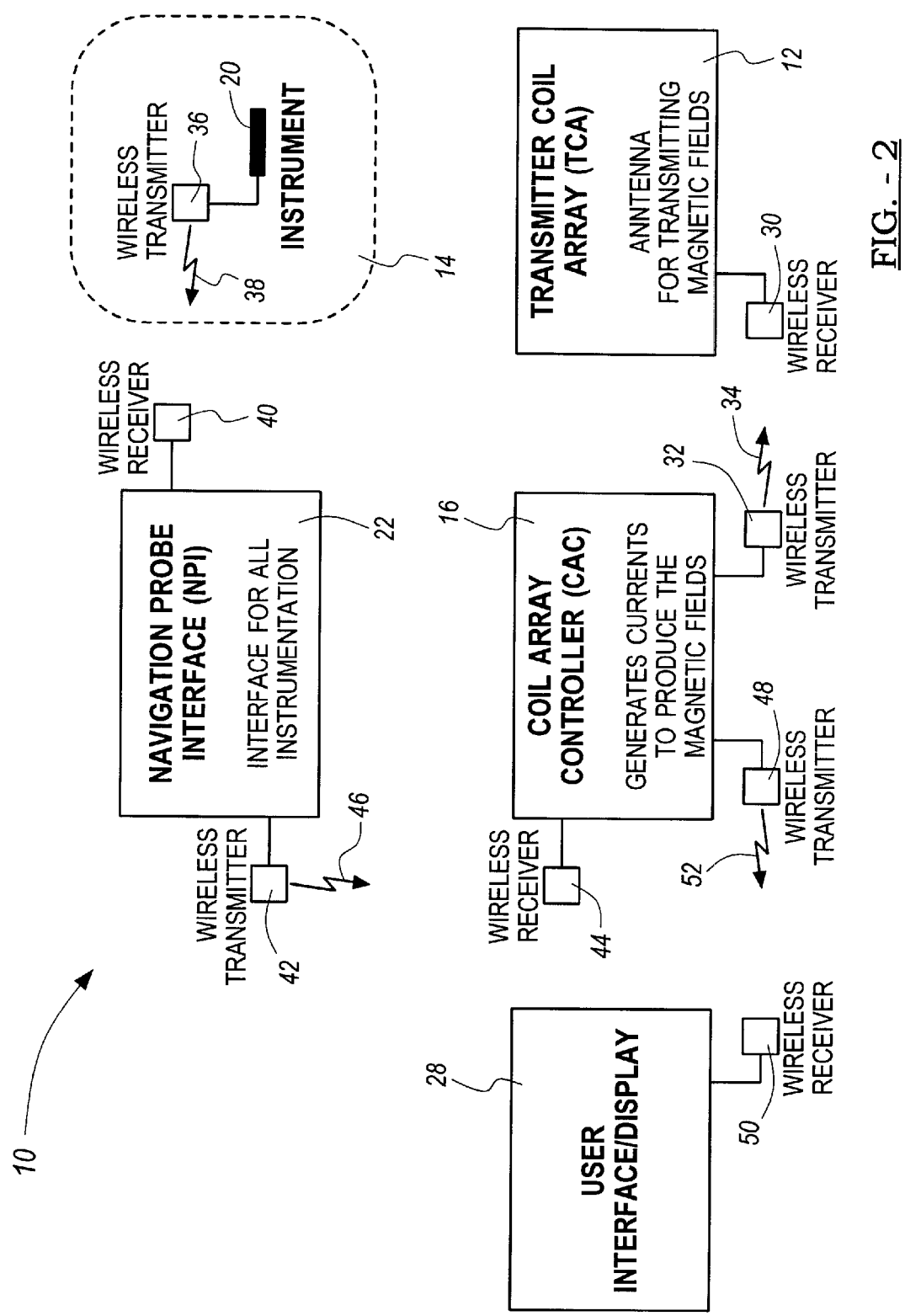
FIG. 2 is an electromagnetic navigation system block diagram according to the teachings of another embodiment of the present invention.

Turning to FIG. 2, the electromagnetic navigation system 10 according to the teachings of another embodiment of the present invention is shown. In this regard, like reference numerals will be used to identify like elements, as set forth in FIG. 1. The electromagnetic navigation system 10 includes the transmitter coil array 12, which is driven by the coil array controller 16 to generate an electromagnetic field or region 14. This electromagnetic field 14 is sensed by the instrument 20 and the navigation probe interface 22 processes the magnetic field strengths sensed by the instrument 20. Again, the navigation probe interface 22 forwards this information to the coil array controller 16, which then determines the position of the instrument 20 in the field or region 14. The location of the instrument 20 is again forwarded to the user interface/display 28 for use by the surgeon during the surgical procedure being performed to provide real time visual feedback of the instrument 20 during the surgical procedure.

The electromagnetic navigation system 10, as shown in FIG. 2, is substantially the same as the electromagnetic navigation system 10, shown in FIG. 1, except that this system employs wireless communications between each element. In this regard, the transmitter coil array 12 includes a wireless receiver 30, which receives control information, via a wireless transmitter 32 coupled to the coil array controller 16. In this configuration, the transmitter coil array 12 will include the amplifiers that are normally positioned in the coil array controller 16 to drive the coils and the coil array controller 16 will simply control the operation of the transmitter coil array 12, via the wireless communication channel 34. Likewise, the instrument 20 includes a wireless transmitter 36 that transmits information over a wireless channel 38 to a wireless receiver 40 in the navigation probe interface 22. The navigation probe interface 22 also includes a wireless transmitter 42, which transmits information to the coil array controller 16, via a wireless receiver 44 over communication channel 46. Finally, the coil array controller 16 forwards navigation information to the user interface/display 28, via a wireless transmitter 48, wireless receiver 50 and wireless channel 52.

The wireless communication or transmission may be accomplished through many types of wireless mediums, such as analog or digital methods. The analog transmission methods may include amplitude modulation (AM), frequency modulation (FM) or phase modulation (PM). Various digital communication standards may also be used such as Ethernet, Blue Tooth or any other type of appropriate digital communication protocol. For example, the wireless communications system, as set forth in Surgical Communications in Power Systems, filed Oct. 28, 1999, U.S. Ser. No. 09/428,722, may be used as one form of wireless communications, which is hereby incorporated by reference. By providing this type of wireless communication of the electromagnetic navigation system 10, as shown in FIG. 2, the transmission lines, as shown in FIG. 1 are substantially eliminated, thereby reducing the amount of cabling required in an operating room environment. This also enables the electromagnetic navigation system 10 to be retrofitted to existing hardware structures without requiring significant modifications to the existing structures. It should further be noted that the electromagnetic navigation system 10 may selectively use both transmission lines and wireless communication.

The electromagnetic navigation system 10 provides significant advantages over existing navigation systems, as discussed above, however, the electromagnetic navigation system 10 must account for electromagnetic navigation near metal objects that may distort the electromagnetic field. This environment typically exists in the operating room and other surgical environments because the metal structure causes or creates distortions in the magnetic field needed for the navigation process. These metal objects, devices or instruments may include, but are not limited to operating room (OR) tables, fluoroscope (C-arms), microscope, ultrasound hand-piece, high-intensity focused ultrasound systems, computer topography imaging (CT), interoperative CT, magnetic resonance imaging (MR), interoperative MR, surgical robot imaging, etc. In order to take into account the distortions caused by such metal objects, the current electromagnetic navigation system 10 may either utilize a shield positioned adjacent to the transmitter coil array 12 to shield the effect of the metal object or the transmitter coil array 12 may be incorporated directly into the metal object and the distortion effect characterized during the calibration process itself since the distortions will generally remain static, further discussed herein.

Figure 5:
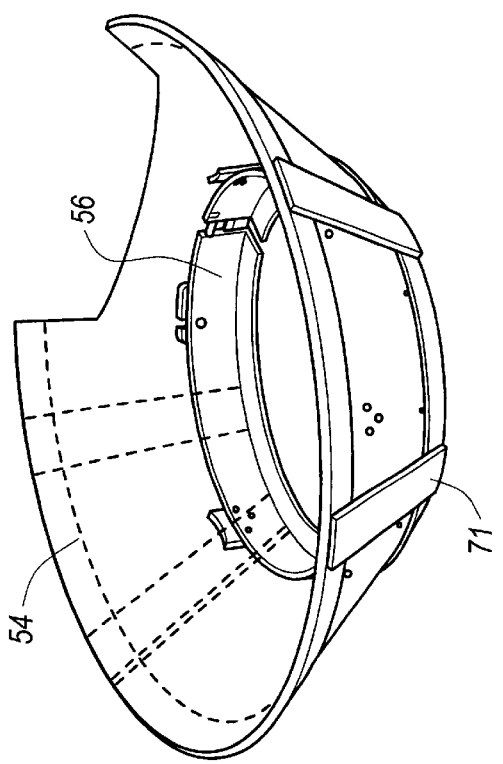
FIG. 5 is a perspective view of a shield having integrated transmitter coils according to the teachings of another embodiment of the present invention.

An exemplary shield 54, shown in FIG. 3, may be used to shield metal objects, such as a fluoroscope (C-arm) (see FIG. 5). The shield 54 is designed to be removably coupled to the C-arm or any other metal object or device requiring shielding by way of a universal band clamp 56. The mounting mechanism or band clamp 56 is able to be adjustably engaged around an intensifier tube 58 of a conventional C-arm 60, which usually has a diameter of about 9 to about 12 inches (see FIG. 5). The shield 54 is substantially conically shaped to substantially reduce or eliminate the effects of the C-arm 60, along with its associated components, such as the intensifier 58. The shield 54 can also be configured in any other shape to create a virtual surface or infinite plane to reflect or shield any type of metal object desired. Reflecting or shielding of these fields prevents field distortion, and thus prevents disturbances by objects on the opposite side of the shield 54.

The shield 54 is formed from a conductive or semi-conductive material, such that the shield's effect on the magnetic field should dominate the effect of the item, such as the C-arm 60 being shielded. The shield 54 may be constructed from materials, such as sheet metal, aluminum, copper, titanium, mu-metal, conductive mylar, etc. The shield 54 may also be formed as a solid shield, a mesh or be modified with holes or slots to reduce the overall weight of the shield 54. Since electromagnetic navigation is generally performed at relatively low frequencies (less than about one megahertz), these frequencies represent long wavelengths that do not pass through the openings, such that the shield 54 essentially acts as a solid shield to these low frequency signals. Therefore, by adding holes or a mesh, the performance of the shield 54 will not be degraded.

Positioned adjacent to or about the periphery of the conically shaped shield 54 is the transmitter coil array 12 which is formed by three sets of transmitting coils 62, which are displaced from the shield 54 by an extension member 64. Each set of transmitting coils 62 consists of three sets of coils 66, each positioned orthogonal to one another and consisting of about fifty wire loops positioned about a cube 68. Offsetting the set of transmitting coils 62 from the shield 54 creates less interference or canceling of the electromagnetic field because of the shield 54 to provide enhanced performance.

Another embodiment of the shield 54 is shown in FIG. 4, where the shield 54 includes three sets of integrally formed transmitting coils 70, also positioned about the perimeter of the shield 54. The transmitting coils 70 are formed substantially adjacent to, or integral with, the shield 54, as opposed to being somewhat displaced from the shield 54, as shown in FIG. 3. While this may create some canceling of the electromagnetic field, this also provides a smaller package should clearance concerns exist in particular applications. The transmitting coils 70 each may include multiple coils configured substantially similar to the set of transmitting coils 62, shown in FIG. 3 or in any other type of configuration. It should further be noted that while the shield 54 shown in FIGS. 3 and 4 include three sets of three orthogonal coils providing for a total of nine coils for navigation purposes, any number of coils or coil configurations may be used. In this regard, generally a minimum of five coils is required to identify the six degrees of freedom (X, Y, Z, angle, azimuth). These coils may be configured with either five transmit coils or more and one receiver coil, or three transmit coils and three receiver coils or any other type of combination. Moreover, should only three degrees of freedom (i.e., X, Y, Z) be desired, only three coils would be required, as is known in the art.

An additional embodiment of the shield 54 is shown in FIG. 5, where the shield includes several integrally formed transmitting coils 71, located about the shield 54. In this regard, the transmitting coils 71 are wrapped and formed integral with the shield 54 with multiple coils extending about the top and bottom perimeter of the shield 54, as well as transmitting coils 71 extending radially from the shield 54. Here again, the coil configuration may be arranged in any manner, as long as each coil has a unique orientation relative to the other coils.

Figure 6:
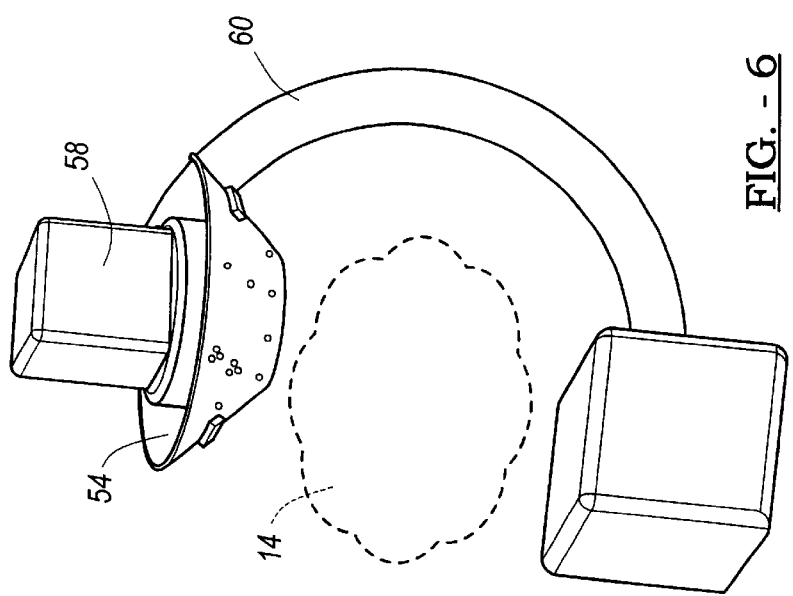
FIG. 6 is a perspective view of a fluoroscope (C-arm) employing the shield of FIG. 4 according to the teachings of the present invention.

Turning briefly to FIG. 6, the C-arm 60 is shown, which incorporates the shield 54 of the electromagnetic navigation system 10 to generate the electromagnetic field or region 14 for navigating the instrument 20. By using the shield 54, which may be formed integral with the C-arm 60, the distortion created by the C-arm 60 is substantially reduced or attenuated so that accurate navigation of the instrument 20 within the region 14 may be achieved. It should further be noted that either the three sets of transmitting coils 62 or the three sets of transmission coils 70 may be incorporated directly into the C-arm 60. With the three sets of transmitting coils 62 and 70 being an integral part of the C-arm 60, the calibration process may be completed with the entire assembly. If the calibration process is completed in this manner, a separate shield is not required. In this embodiment, the effect of distortion caused by the C-arm 60 or any other metal object on the transmitted fields, would be taken into account and characterized during the calibration process and since these distortions are generally static, accurate navigation is achieved.

Figure 7:
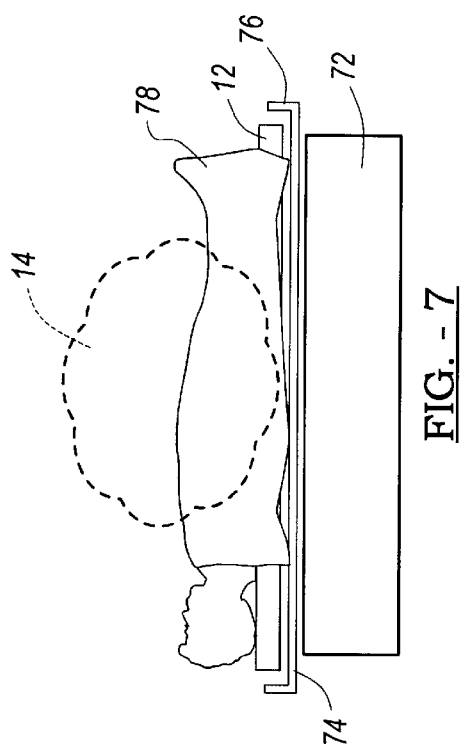
FIG. 7 is a side view of an operating room (OR) table having a transmitter coil array (TCA) positioned atop the OR table with a shield positioned between the OR table and transmitter coil array (TCA) according to the teachings of another embodiment of the present invention.
Figure 8:
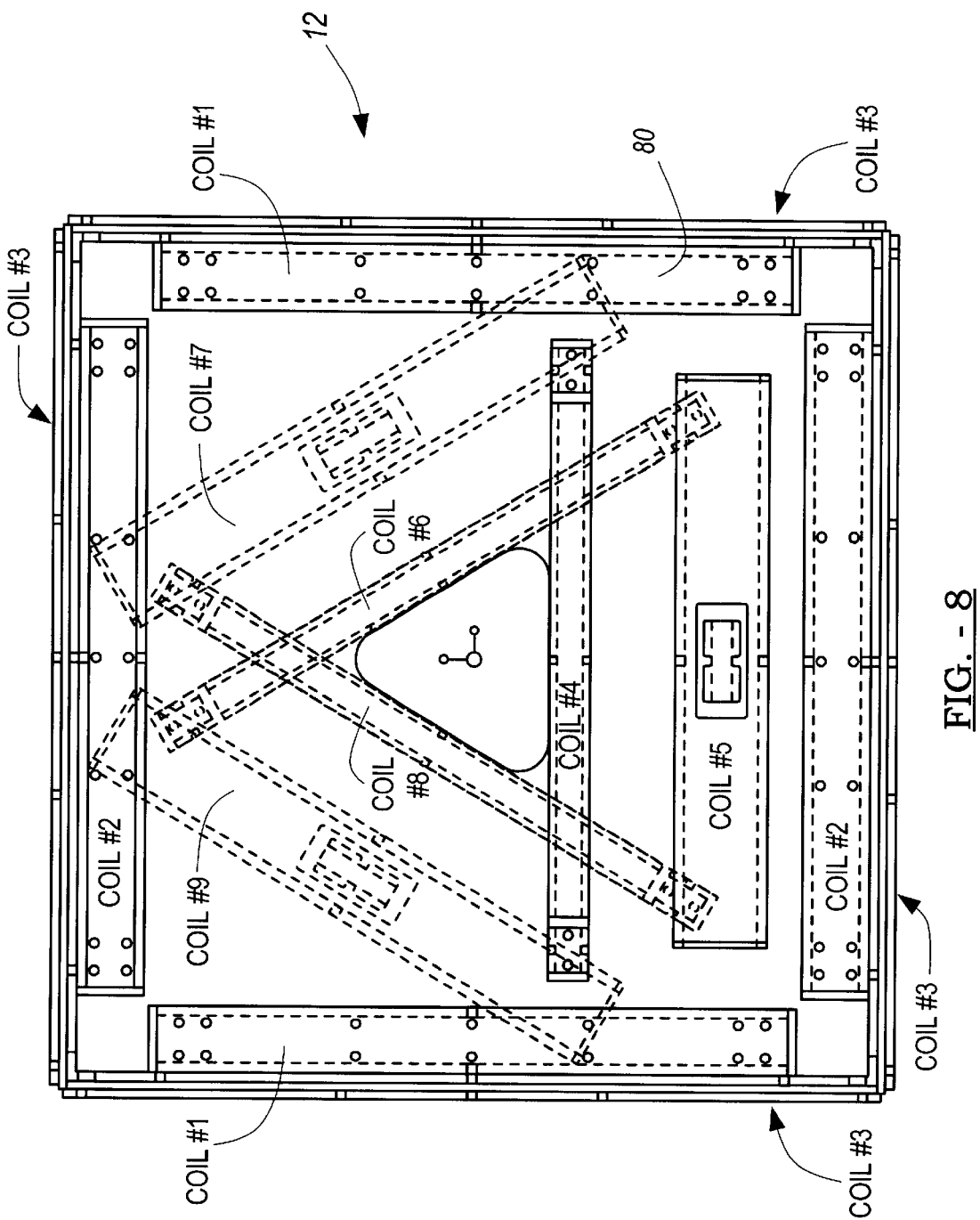
FIG. 8 is a diagram illustrating the transmitter coil array configuration of FIG. 7 in further detail.

Referring to FIGS. 7 and 8, another embodiment of the transmitter coil array 12 is shown incorporated over an operating room (OR) table 72. Positioned between the transmitter coil array 12 and the operating room table 72 is a planar shield 74 having an upturned peripheral lip 76. The shield 74 again acts as an infinite plane to reflect and shield the electromagnetic field or region 14 generated by the transmitter coil array 12 from the metal operating room table 72. The upturned lip 76 also directs the electromagnetic field or region 14 in the vicinity of the patient 78. The OR table 72, shield 74 and transmitter coil array 12 may be separate components or attached to one another.

The configuration of the transmitter coil array 12 used with the OR table is shown in further detail in FIG. 8. The transmitter coil array 12 includes nine discrete coils 80 positioned about the transmitter coil array 12. Each coil 80 is located or positioned at a different orientation relative to the remaining coils 80, such that each coil 80 generates its own unique electromagnetic field. Three sets of coils 80 are generally driven at a time so that there are three sets of three coils 80 driven sequentially with each coil 80 in each set of three driven at its own unique frequency to identify that particular field. Here again, other types of coil arrangements and numbers of coils may be utilized in the electromagnetic navigation system 10. Moreover, as shown herein, the transmitter coil array 12 may be configured in any number of ways to accommodate for its particular application and the use in association with the C-arm 60 and the OR table 72 are merely exemplary in nature.

Figure 9:
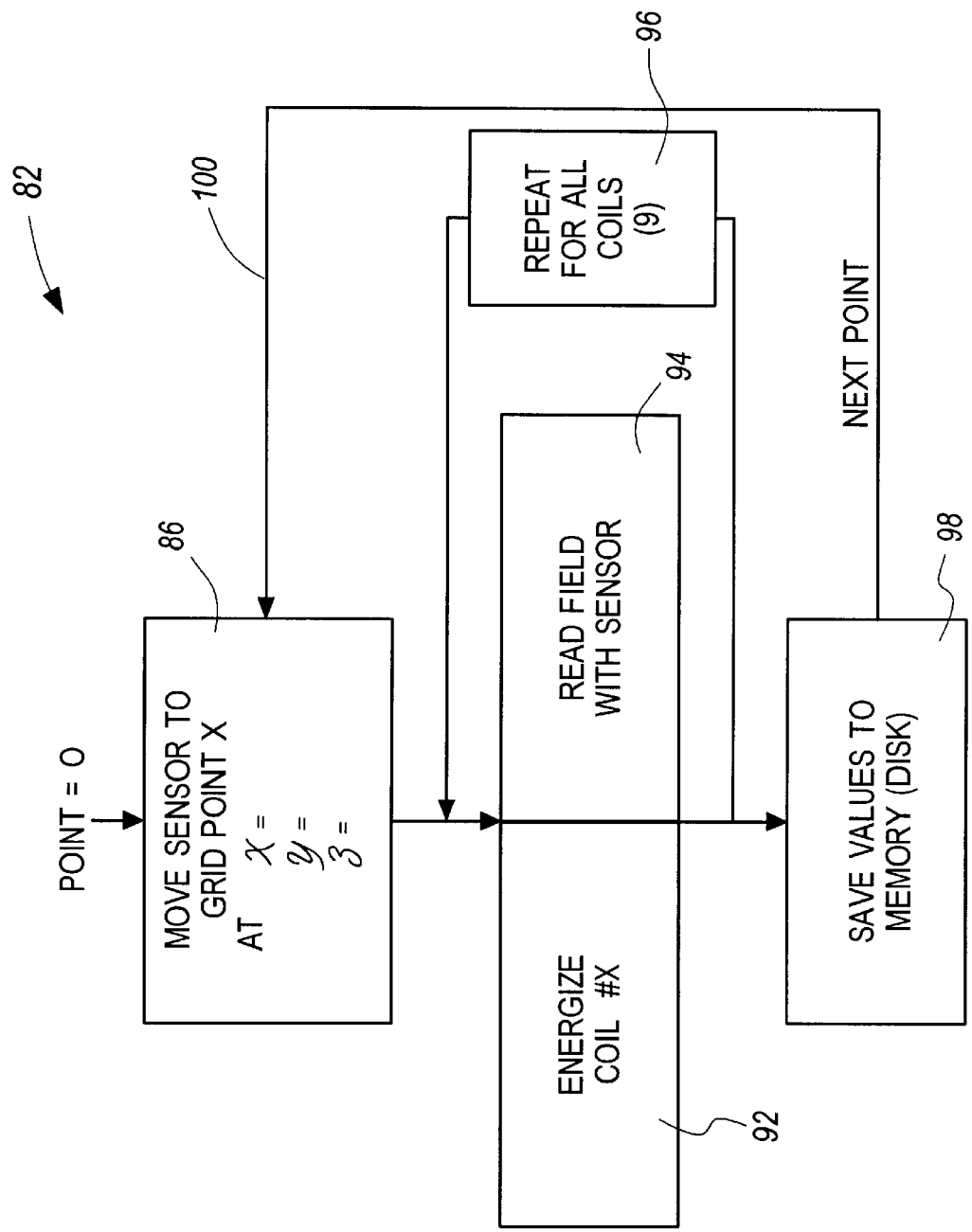
FIG. 9 is an illustration of a calibration process according to the teachings of the present invention.
Figure 10:
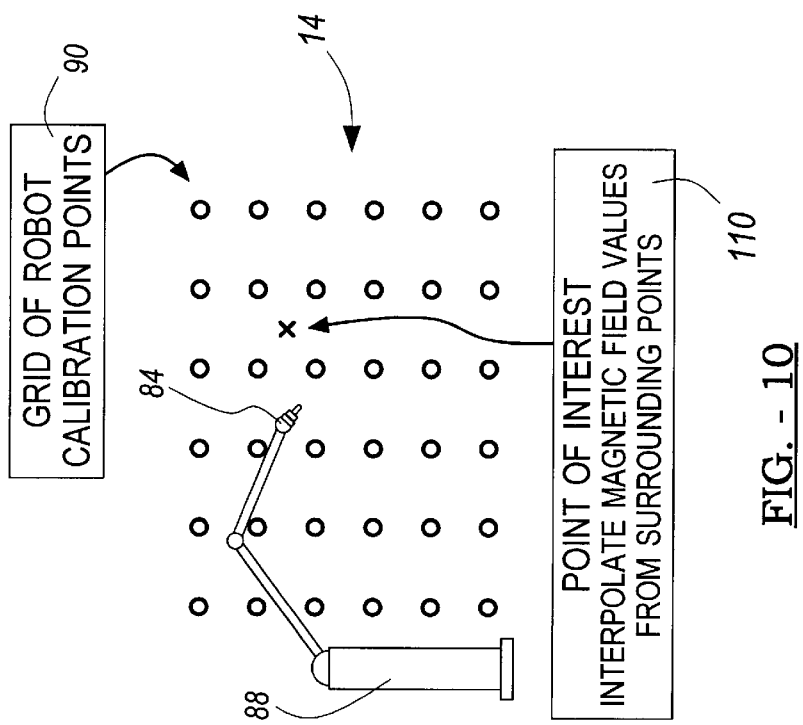
FIG. 10 is a two dimensional grid of robotically measured calibration points used in the calibration process according to the teachings of the present invention.

Turning now to FIGS. 9 and 10, the calibration process 82 according to the teachings of the present invention is disclosed in further detail. The calibration process 82 is conducted at the factory and is implemented by simulating the environment in which the electromagnetic navigation system 10 will be employed. In this regard, should a shield 56 or 74 be used, as is shown in FIGS. 6 and 7, that particular configuration with the C-arm 60 or the OR table 72 will be calibrated at the factory prior to shipment of the electromagnetic navigation system 10 to characterize the effects of the particular metal object or surgical device being used. Likewise, should the transmitter coil array 12 be integrally formed or incorporated directly into the surgical device having metallic portions rather than retrofitting the surgical device with the shield, the surgical device with the incorporated electromagnetic navigation system 10 will also be calibrated prior to shipment or delivery. This calibration process 82 assumes that the distortion from the metal object or device will remain static.

The calibration process 82 starts by moving a calibration sensor 84 to a point in the electromagnetic field or region 14 at step 86. Preferably, the starting point will be identified as the origin (i.e., equals zero) and all other measured points will be referenced back to this origin. In this regard, a robotic calibration arm or unit 88 having the calibration sensor 84 (see FIG. 10) is employed to measure the magnetic field strength of each energized coil, along a pre-determined grid of calibration points 90. As shown in FIG. 10, a two-dimensional grid is illustrated having a plurality of calibration grid points 90 disposed equally throughout the two-dimensional grid. For example, each grid point 90 may be separated every 15 millimeters. During the calibration process 82, a three-dimensional grid will be employed to measure the magnetic field strength of each calibration point 90 throughout the region 14 for each coil in the transmitter coil array 12. For example, a one meter cubed (m$^3$) region 14 may be separated into several calibration grid points 90, such as eight thousand grid points 90, which are sensed by the calibration sensor 84 on the robotic unit 88 as the calibration sensor 84 is positioned at each one of these discrete grid points 90.

Referring back to FIG. 9, with the calibration sensor 84 positioned at the first grid point 90 or origin at step 86, one of the coils in the transmitter coil array 12 is energized at step 92 and the magnetic field strength generated is sensed or read at this grid point 90 with the calibration sensor 84 at step 94. Again, the navigation probe interface 22 instructs the coil array controller 16 to drive a particular coil in the transmitter coil array 12. With the magnetic field sensed by the calibration sensor 84, the magnetic field strength is determined for that particular calibration point 90 by the navigation probe interface 22. Each coil in the transmitter coil array 12 is then driven by the coil array controller 16 at that particular calibration point 90, via step 96. With the magnetic field strength values known for each coil in the transmitter coil array 12, these magnetic field strengths are then stored to memory at step 98. In this regard, these magnetic field strengths are forwarded from the navigation probe interface 22 through the general purpose computer in the control array controller 16 and stored on a flash ROM or any other type of memory housed within the transmitter coil array 12. In this way, the transmitter coil array 12 may be operated by any coil array controller 16, since the calibration values are stored with the transmitter coil array 12.

The calibration process 82 continues by moving to a next calibration point 90 at step 100 to again determine the magnetic field strengths from each coil. With the navigation probe interface 22 synchronizing the coil array controller 16 to drive each coil in the transmitter coil array 12 and with the robotic unit 88 positioning the calibration sensor 84 at each calibration point 90 within the three-dimensional calibration grid, the calibration process 82 continues until all of the field strengths for all of the coils at each calibration point 90 in the calibration grid is stored. Accordingly, the calibration process 82 stores actual measurements of the magnetic field strength generated by the transmitter coil array 12, while taking into account or characterizing the distortion effects of either the particular shield, coupled to the surgical device or the transmitter coil array 12 incorporated directly into the surgical device. In this way, any metallic distortions caused by the metal object or device, such as the C-arm 60 or the OR table 74 is taken into account by performing the real time measurements with these objects in place. Therefore, any distortions caused by utilizing the electromagnetic navigation system 10 in its environment are already accounted for during the factory calibration process to provide accurate navigation of the instrument.

Figure 12:
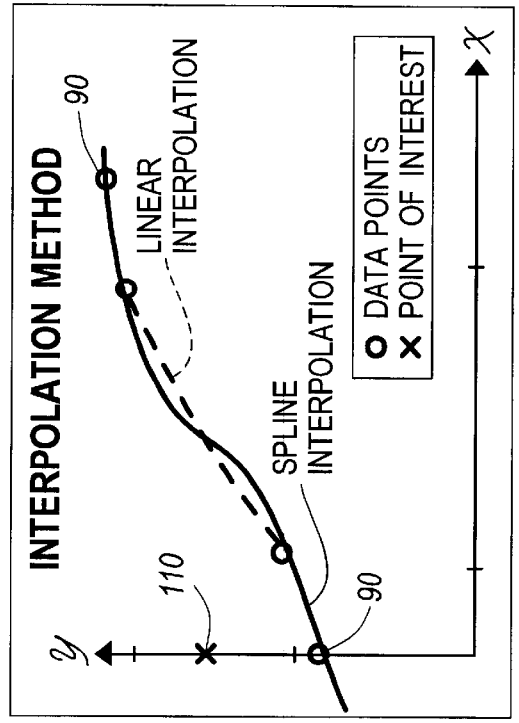
FIG. 12 is a graph illustrating two interpolation methods utilized in the navigation process according to the teachings of the present invention.
Figure 11:
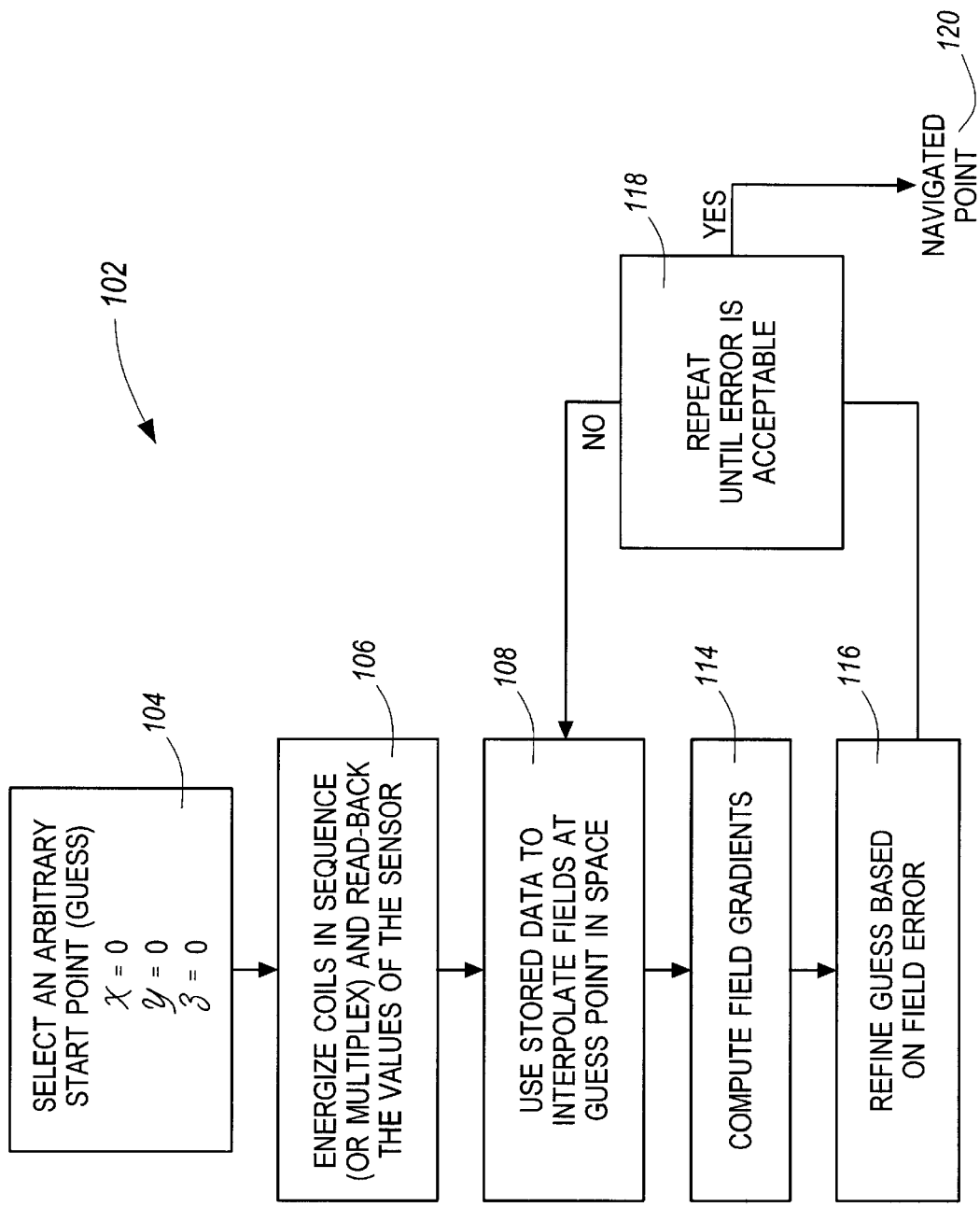
FIG. 11 is an illustration of a navigation process according to the teachings of the present invention.

Referring now to FIGS. 10–12, the navigation process 102 will be described in further detail. The navigation process 102 is a minimization process, as is known in the art, such as Newton's method, which begins at step 104. At step 104, an arbitrary starting point is selected, which is generally the center of volume of the region 14 (i.e., 0, 0, 0). Once the arbitrary start point or guess point 110 is selected at step 104, the navigation process 102 continues to step 106 where the coils in the transmitter coil array 12 are energized, either sequentially or by frequency multiplexing and the magnetic field strength values are received by the sensor located in the instrument 20. Once these values are determined at step 106, the navigation process continues to step 108 where the previously stored calibration data or field strengths for the calibration points 90 in the calibration grid are used to interpolate the fields at the guess point 110 in space. In this regard, should the guess point 110 not be one of the known calibration grid points 90, the guess point 110 is interpolated using known interpolation techniques. These techniques, for example, may include linear interpolation or spline interpolation as shown in FIG. 12. The location of the guess point 110 may be determined from the known calibration grid points 90 using these known interpolation methods to determine the magnetic field strengths between the known calibration grid points 90. Additionally, any other type of interpolation method may also be used such as polynomial curve fitting, etc.

Once the field strengths are determined for the guess point 110 at step 108, the navigation process 102 continues to step 114 where computation of the field gradients or the difference in field strengths between the guess point 110 and the measured fields at the instrument location are determined. These field gradients or errors are then used at step 116 to refine the guess point 110 during the minimization process to select a new guess point 110 which is closer to the actual sensor location. Once the refined guess point 110 is determined, this process is continued without requiring additional measurements from the instrument 20 until the error between the guess point 110 and the actual instrument location is minimized to an acceptable value at step 118. If the error value is not acceptable, the navigation process 102 again continues with a new guess point 110 selected which is closer to the actual instrument location and the error again computed, via the steps in blocks 108, 114 and 116. Should the error be acceptable, as determined in step 118, the navigation process 102 ends with the guess point 110 now representing the actual instrument location or navigated point 120. In this way, navigation of the instrument 20 is performed very accurately without having metal objects effect the overall navigation since the calibration process has already taken into effect the metal object during creation of the look-up table for the calibration grid points 90, which is used during the navigation process 102.

Figure 13:
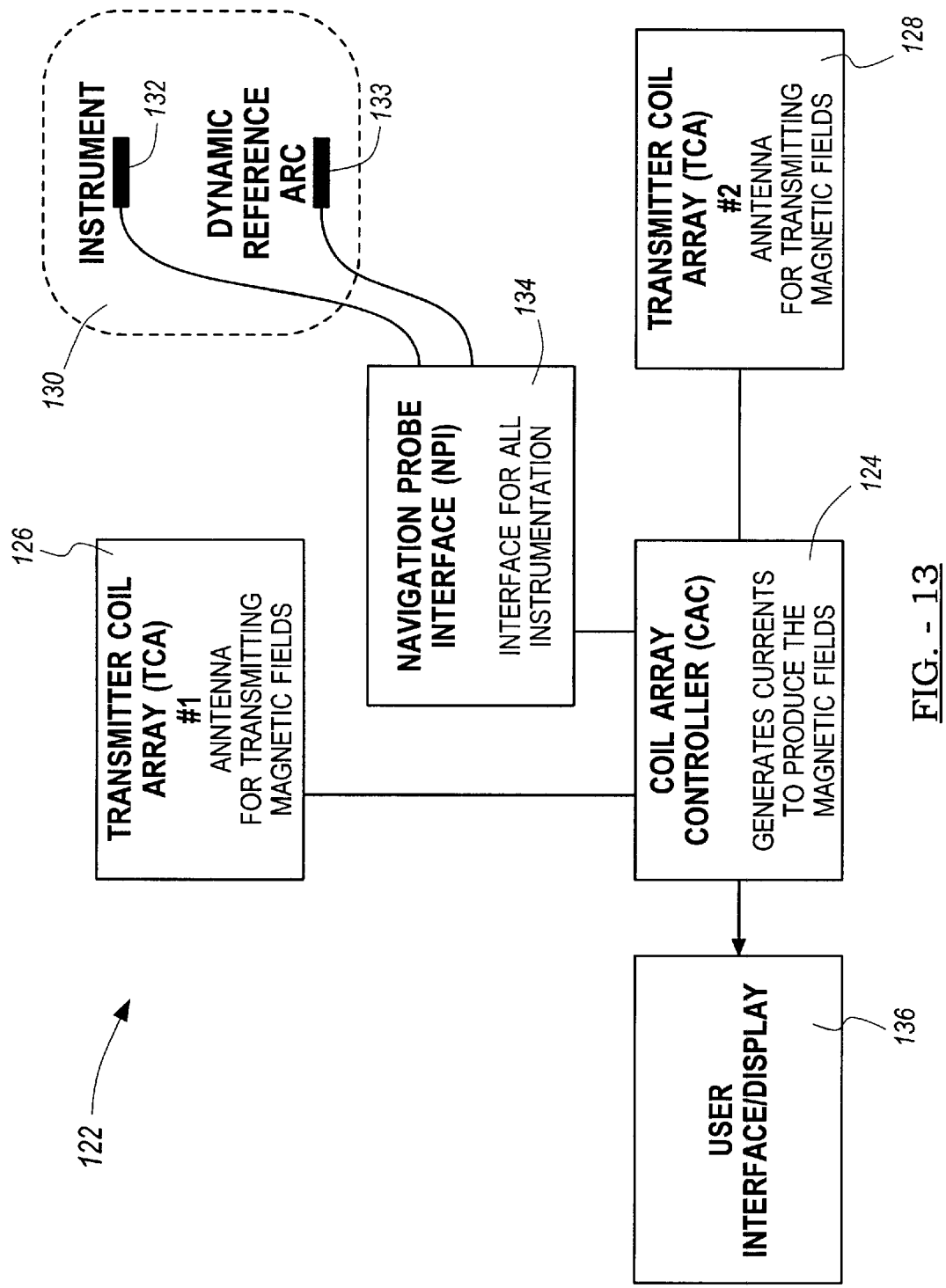
FIG. 13 is an electromagnetic navigation system block diagram according to the teachings of another embodiment of the present invention.
Figure 14:
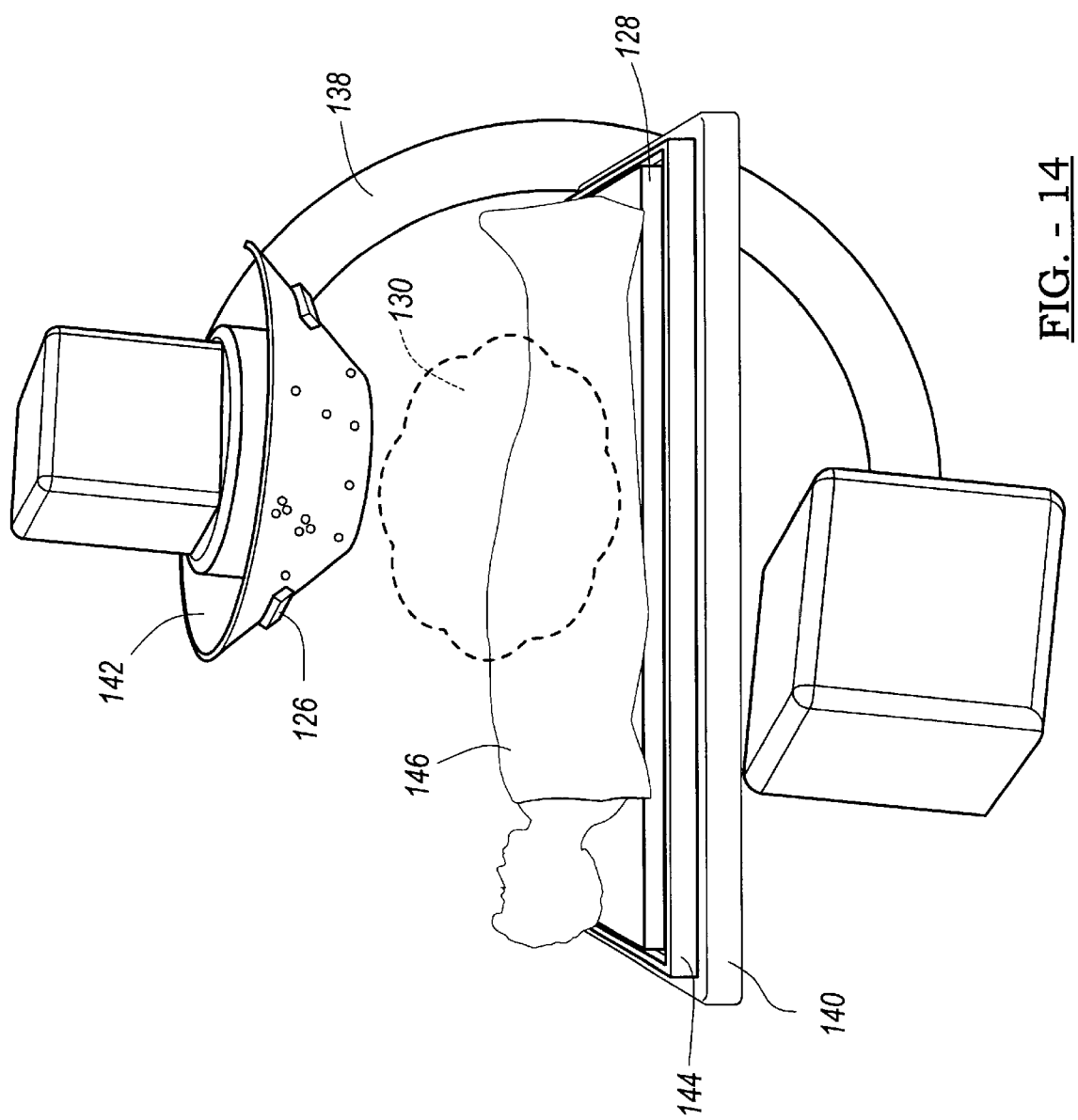
FIG. 14 illustrates the electromagnetic navigation system of FIG. 13 associated with a fluoroscope (C-arm) and an OR table.

Finally, referring to FIGS. 13 and 14, an electromagnetic navigation system 122 according to the teachings of another embodiment of the present invention is shown. The electromagnetic navigation system 122 is substantially similar to the electromagnetic navigation systems 10, shown in FIGS. 1 and 2, except that the electromagnetic navigation system 122 includes an additional transmitter coil array and a dynamic reference arc. In this regard, the electromagnetic navigation system 122 includes a coil array controller 124 which drives a first transmitter coil array 126, as well as a second transmitter coil array 128. Both transmitter coil arrays 126 and 128 generate an electromagnetic field or region 130 where the instrument 132 is navigated and a dynamic reference arc 133 is positioned. Here again, instrument 132 provides the received magnetic field strengths to navigation probe interface 134 for processing and forwarding to the coil array controller 124 and the dynamic reference arc 133 is used for a reference by the instrument 132, further discussed herein. The coil array controller 124 again forwards the navigation information to a user interface/display 136 for use during the surgical procedure being performed.

The electromagnetic navigation system 122 is shown configured in FIG. 14 in association with a C-arm 138 and an OR table 140. Here again, the transmitter coil array 126 may be configured within shield 142 of the C-arm 138 or incorporated directly into the C-arm 138. The transmitter coil array 128 is shown positioned above the OR table 140 with a shield 144 positioned therebetween.

By providing both the transmitter coil array 126 and the transmitter coil array 128 to generate the electromagnetic field or region 130 about the patient 146, each transmitter coil array 126 and 128 may be driven simultaneously, sequentially or independent from one another. In this regard, the coil array controller 124 is capable of driving the transmitter coil arrays 126 and 128 simultaneously at different frequencies so that the particular fields may be identified. Alternatively, the transmitter coil arrays 126 and 128 may be time multiplexed or driven sequentially, via the coil array controller 124. In other situations, it may be desirable to initially drive the transmitter coil array 126 located on the C-arm 138 during the surgical procedure while the C-arm 38 generates a fluoroscopic image. However, the C-arm 138 may be in the way for certain portions of the surgical procedure. If so, the C-arm 138 may be rotated or moved our of the way after the image is captured to provide for further surgical clearance while still conducting navigation, via the second transmitter coil array 128 associated with the OR table 140.

In this way, navigation handoff can be performed between both transmitter coil arrays 126 and 128 without requiring the surgeon to have to stop during the overall surgical procedure should one of the particular metal or surgical instruments be in the way. The dynamic reference arc 133 is substantially similar to the instrument 132 in that it includes receive coils capable of providing six degrees of freedom information. However, the dynamic reference arc 133 is used as a reference and is fixed relative to the patient being navigated to provide a reference point for the instrument 132. In other words, the instrument 132 may be referenced back to either transmitter coil array 126 or 128 and the dynamic reference arc 133 may be also referenced back to the transmitter coil arrays 126 and 128 to determine the relative positions of each. By having this information, the instrument 132 may then be simply referenced back to the dynamic reference arc 133 by simple subtraction of the fields, as is known in the art, which removes the transmitter coil arrays 126 and 128 out of the calculation process, thereby enabling unobstructed hand-offs between the transmitter coil array 126 and the transmitter coil array 128. Use of the dynamic reference arc 133 may also be employed with the navigation system 10, shown in FIGS. 1 and 2 should this be desired. An example of such hand off technology is set forth in System For Translation of Electromagnetic and Optical Localization Systems, filed Oct. 28, 1999, U.S. Ser. No. 09/429,568, which is hereby incorporated by reference. Moreover, it should be further noted that the calibration process 82 will be performed with both the C-arm 138 and the OR table 140 in proximity to one another, as shown in FIG. 14 to take into effect the entire surgical environment, thereby providing further accuracy and surgical versatility.

The electromagnetic navigation systems 10 and 122, therefore, provide for very accurate surgical navigation of the instruments 20 and 132 during the surgical procedure because the calibration process 82 takes into account and characterizes the distortion effect of the surgical device used during the surgical procedure. This accuracy is achieved by using the information determined during the calibration process 82 in the navigation process 102. In this way, accurate navigation of the instruments 20 and 132 are achieved in an efficient, cost effective and versatile manner that also takes into effect the tolerance of the transmitter coil array and the surrounding environment.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An electromagnetic navigation system for use in navigating a probe through an electromagnetic field positioned near a C-arm, said electromagnetic navigation system comprising:

a transmitter coil array having a plurality of transmitter coils, said transmitter coil array operable to generate the electromagnetic field to navigate the probe; and a shield attached to the C-arm, said shield operable to substantially shield the C-arm from the electromagnetic field generated by said transmitter coil array, wherein said shield substantially reduces distortion of the electromagnetic field by the C-arm, thereby enabling accurate navigation of the probe in the electromagnetic field.

2. The electromagnetic navigation system as defined in claim 1 wherein said shield is attached to the C-arm by a mounting mechanism.

3. The electromagnetic navigation system as defined in claim 2 wherein said mounting mechanism is formed by an adjustable band clamp.

4. The electromagnetic navigation system as defined in claim 1 wherein said shield is formed from one of a conductive and semi-conductive material.

5. The electromagnetic navigation system as defined in claim 4 wherein said shield is formed from a material selected from a group consisting of sheet metal, aluminum, copper, titanium, mu-metal, and conductive mylar.

6. The electromagnetic navigation system as defined in claim 1 wherein said shield is formed as a solid shield.

7. The electromagnetic navigation system as defined in claim 1 wherein said shield is formed as a mesh.

8. The electromagnetic navigation system as defined in claim 1 wherein said shield is formed with a plurality of holes.

9. The electromagnetic navigation system as defined in claim 1 wherein said transmitter coil array is attached to said shield.

10. The electromagnetic navigation system as defined in claim 9 wherein said transmitter coil array is integrated into said shield.

11. The electromagnetic navigation system as defined in claim 9 wherein said transmitter coil array is displaced from said shield.

12. The electromagnetic navigation system as defined in claim 1 further comprising a coil array controller operable to drive the transmitter coil array and a navigation probe interface operable to receive magnetic field strengths sensed by the probe.

13. The electromagnetic navigation system as defined in claim 12 further comprising a second transmitter coil array having a plurality of transmitter coils, said second transmitter coil array operable to generate the electromagnetic field to navigate the probe.

14. The electromagnetic navigation system as defined in claim 13 wherein said transmitter coil array and said second transmitter coil array are driven simultaneously by said coil array controller.

15. The electromagnetic navigation system as defined in claim 13 wherein said transmitter coil array and said second transmitter coil array are driven sequentially by said coil array controller.

16. The electromagnetic navigation system as defined in claim 12 further comprising wireless communications between said transmitter coil array, said coil array controller, and said navigation probe interface.

17. The electromagnetic navigation system as defined in claim 1 wherein said shield has a shape selected from a group consisting of conical and planar.

18. The electromagnetic navigation system as defined in claim 1 wherein said transmitter coil array includes a plurality of sets of transmitter coils.

19. The electromagnetic navigation system as defined in claim 1 wherein each of said plurality of transmitter coils are driven sequentially in a time multiplexed manner.

20. The electromagnetic navigation system as defined in claim 1 wherein said plurality of transmitter coils are driven simultaneously with each transmitter coil driven at a unique frequency.

21. The electromagnetic navigation system as defined in claim 1 further comprising a user interface/display unit operable to display a location of the probe navigating through the electromagnetic field.

22. The electromagnetic navigation system as defined in claim 13 further comprising a second shield positioned adjacent said second transmitter coil array.

23. The electromagnetic navigation system as defined in claim 1 wherein said shield includes an up-turned peripheral lip.

24. The electromagnetic navigation system as defined in claim 1 wherein the C-arm generates a fluoroscopic image while said transmitter coil array simultaneously generates the electromagnetic field to navigate the probe.

25. The electromagnetic navigation system as defined in claim 1 wherein said shield is formed integral with the C-arm.

26. An electromagnetic navigation system for use in navigating a probe through an electromagnetic field during a surgical procedure, said electromagnetic navigation system comprising:
    a metal instrument used during the surgical procedure, said metal instrument formed at least in part by metallic material; and
    a transmitter coil array having a plurality of transmit coils, said transmitter coil array operable to generate the electromagnetic field used to navigate the probe, said transmitter coil array integrated and incorporated directly into said metal instrument, wherein effects of metallic distortion on the electromagnetic field by said metal instrument is characterized during a calibration process to provide substantially accurate navigation of the probe during the surgical procedure.

27. The electromagnetic navigation system as defined in claim 26 wherein said metal instrument is selected from a group consisting of an operating room (OR) table, a fluoroscope (C-arm), a microscope, an ultrasound hand piece, a high-intensity focused ultrasound systems, a computer tomography imaging system (CT), an intraoperative computer tomography system, a magnetic resonance imaging system (MRI), an intraoperative magnetic resonance system and surgical robot, whereby said transmitter coil array is incorporated directly into said selected metal instrument.

28. The electromagnetic navigation system as defined in claim 26 further comprising a coil array controller operable to drive the transmitter coil array and a navigation probe interface operable to receive magnetic field strengths sensed by the probe.

29. The electromagnetic navigation system as defined in claim 28 further comprising a second transmitter coil array having a plurality of transmitter coils, said second transmitter coil array operable to generate the electromagnetic field to navigate the probe.

30. The electromagnetic navigation system as defined in claim 29 where in said transmitter coil array and said second transmitter coil array are driven simultaneously by said coil array controller.

31. The electromagnetic navigation system as defined in claim 29 wherein said transmitter coil array and said second transmitter coil array are driven sequentially by said coil array controller.

32. The electromagnetic navigation system as defined in claim 28 further comprising wireless communications between said transmitter coil array, said coil array controller, and said navigation probe interface.

33. The electromagnetic navigation system as defined in claim 26 further comprising a user interface/display unit operable to display a location of the probe navigating through the electromagnetic field.

34. The electromagnetic navigation system as defined in claim 26 wherein said transmitter coil array includes a plurality of sets of transmitter coils.

35. The electromagnetic navigation system as defined in claim 26 wherein each of said plurality of transmitter coils are driven sequentially in a time multiplexed manner.

36. The electromagnetic navigation system as defined in claim 26 wherein said plurality of transmitter coils are driven simultaneously with each transmitter coil driven at a unique frequency.

37. The electromagnetic navigation system as defined in claim 26 wherein said transmitter coil array is integrated and incorporated directly into a shield integrally formed with said metal instrument.

38. An electromagnetic navigation system for use in navigating a probe through an electromagnetic field positioned near a first metal object and a second metal object, said electromagnetic navigation system comprising:
    a first transmitter coil array having a plurality of transmitter coils, said first transmitter coil array operable to generate a first electromagnetic field to navigate the probe;

a first shield positioned adjacent the first metal object, said first shield operable to substantially shield the first metal object from the electromagnetic field generated by said first transmitter coil array, wherein said first shield substantially reduces distortion of the electromagnetic field by the first metal object;

a second transmitter coil array having a plurality of transmitter coils, said second transmitter coil array operable to generate a second electromagnetic field to navigate the probe; and a second shield positioned adjacent the second metal object, said second shield operable to substantially shield the second metal object from the electromagnetic field generated by said second transmitter coil array, wherein said second shield substantially reduces distortion of the electromagnetic field by the second metal object.

39. The electromagnetic navigation system as defined in claim 38 wherein the first metal object is a C-arm and the second metal object is an OR table.

40. The electromagnetic navigation system as defined in claim 39 wherein said first shield is a conically shaped shield attached to said C-arm and said second shield is a substantially planar shield positioned above the OR table.

41. The electromagnetic navigation system as defined in claim 40 wherein said first conically shaped shield is formed integral with said C-arm and said second substantially planar shield is formed integral with said OR table.

42. The electromagnetic navigation system as defined in claim 40 wherein said substantially planar shield includes an up-turned peripheral lip.

43. The electromagnetic navigation system as defined in claim 39 wherein said C-arm generates a fluoroscopic image while said first transmitter coil array simultaneously generates said first electromagnetic field to navigate the probe.

44. The electromagnetic navigation system as defined in claim 38 wherein the first and second metal objects are selected from a group comprising an OR table, a fluoroscope (C-arm), a microscope, an ultrasound hand piece, a high-intensity focused ultrasound system, a computer tomography imaging system (CT), an intraoperative computer tomography system, a magnetic resonance imaging system (MRI), an intraoperative magnetic resonance imaging system, and a surgical robot.

45. The electromagnetic navigation system as defined in claim 38 wherein first and second shields are formed from one of a solid shield and a mesh.

46. The electromagnetic navigation system as defined in claim 38 wherein said first and second transmitter coil arrays are driven simultaneously by a coil array controller.

47. The electromagnetic navigation system as defined in claim 38 wherein said first and second transmitter coil arrays are driven sequentially by a coil array controller.

48. An electromagnetic navigation system for use in navigating a probe through an electromagnetic field positioned near a metal object, said electromagnetic navigation system comprising:

a transmitter coil array having a plurality of transmitter coils, said transmitter coil array operable to generate the electromagnetic field to navigate the probe; and a shield positioned adjacent the metal object, said shield operable to substantially shield the metal object from the electromagnetic field generated by said transmitter coil array, said transmitter coil array being integrally formed with said shield, wherein said shield substantially reduces distortion of the electromagnetic field by the metal object, thereby enabling accurate navigation of the probe in the electromagnetic field.

49. The electromagnetic navigation system as defined in claim 48 wherein said shield is a conically shaped shield.

50. The electromagnetic navigation system as defined in claim 49 wherein said transmitter coils extend about a top and bottom perimeter of said conically shaped shield and extend radially from said conically shaped shield.

51. The electromagnetic navigation system as defined in claim 48 wherein said shield has a shape selected from one of either conical and planar.

52. The electromagnetic navigation system as defined in claim 49 wherein the metal object is a C-arm and wherein said conically shaped shield is attached to the C-arm.

53. The electromagnetic navigation system as defined in claim 49 wherein the metal object is a C-arm and wherein said conically shaped shield is formed integral with the C-arm.

54. The electromagnetic navigation system as defined in claim 48 wherein said shield is substantially planar and includes a peripheral up-turned lip.

55. The electromagnetic navigation system as defined in claim 48 wherein the metal object is a C-arm, whereby said C-arm generates a fluoroscopic image while said transmitter coil array simultaneously generates the electromagnetic field to navigate the probe.

* * * * *